US008623424B2

(12) United States Patent
Wu et al.

(10) Patent No.: US 8,623,424 B2
(45) Date of Patent: Jan. 7, 2014

(54) TRADITIONAL CHINESE MEDICINAL COMPOSITIONS FOR TREATING DEPRESSION, FORMULATION THEREOF, METHOD FOR PREPARING THE SAME THEREOF

(75) Inventors: Yiling Wu, Shijiazhuang (CN); Huang Huang, Shijiazhuang (CN)

(73) Assignee: Hebei Yiling Medicine Research Institute Co., Ltd. (CN)

( * ) Notice: Subject to any disclaimer, the term of this patent is extended or adjusted under 35 U.S.C. 154(b) by 909 days.

(21) Appl. No.: 12/160,722

(22) PCT Filed: Jan. 11, 2007

(86) PCT No.: PCT/CN2007/000109
§ 371 (c)(1),
(2), (4) Date: Sep. 28, 2012

(87) PCT Pub. No.: WO2007/079691
PCT Pub. Date: Jul. 19, 2007

(65) Prior Publication Data
US 2010/0272837 A1    Oct. 28, 2010

(30) Foreign Application Priority Data
Jan. 11, 2006    (CN) .......................... 2006 1 0000657

(51) Int. Cl.
*A61K 36/00*    (2006.01)
(52) U.S. Cl.
USPC ....................................................... 424/725
(58) Field of Classification Search
USPC ....................................................... 424/725
See application file for complete search history.

(56) References Cited

U.S. PATENT DOCUMENTS

| | | | | |
|---|---|---|---|---|
| 6,280,751 | B1 * | 8/2001 | Fletcher et al. | 424/401 |
| 2002/0031559 | A1 * | 3/2002 | Liang et al. | 424/725 |
| 2004/0241253 | A1 * | 12/2004 | Ikeda et al. | 424/725 |
| 2006/0018867 | A1 * | 1/2006 | Kawasaki et al. | 424/70.122 |

FOREIGN PATENT DOCUMENTS

| | | |
|---|---|---|
| CN | 1232694 A | 10/1999 |
| CN | 1167454 C | 9/2004 |
| CN | 1216620 C | 8/2005 |

OTHER PUBLICATIONS

Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*
Mirror of Health, People's Medical Publishing House, 2007, Beijing, China, p. 195.*
Gershenfeld et al. Looking Forward in Geriactric Anxiety and Depression; The American Journal of Geriatric Psychiatry; Dec. 2005; 13, 12, pp. 1027-1040.*
International Search Report, Apr. 2007.

* cited by examiner

*Primary Examiner* — Patricia Leith
(74) *Attorney, Agent, or Firm* — Banner & Witcoff, Ltd.

(57) ABSTRACT

The present invention relates to a traditional Chinese medicinal composition for treating depression, which has a significant therapeutic effect and comprises as active components Fructus Gardeniae, Fructus Forsythiae, Rhizoma Pinelliae, and Cortex Magnoliae Officinalis. The present invention further concerns a method for the preparation of the composition, as well as a pharmaceutical formulation containing the composition.

20 Claims, No Drawings

TRADITIONAL CHINESE MEDICINAL COMPOSITIONS FOR TREATING DEPRESSION, FORMULATION THEREOF, METHOD FOR PREPARING THE SAME THEREOF

TECHNICAL FIELD

The present invention relates to traditional Chinese medicinal compositions for treating depression, formulation thereof, method for preparing the same and application thereof.

BACKGROUND OF THE INVENTION

Depression disorder is one of the most common mental disorders in the human beings. The research by World Health Organization (WHO) indicates that the incidence of depression in the world is about 3.1%. In western developed countries, the incidence of lifelong depression ranged from 6% to 8%. Along with the gradual aging of the population, the incidence of depression in the population of more than 60 years old would be as high as 20%-50%. It was predicted that the incidence of depression in these countries would rise to about 8%-10% in 2005. It was indicated in *World Health Report,* 2002 issued by WHO that depression had been the fourth severest disease in the world, and would become the second severest disease next to heart attack in 2020 (ZHU Ziqing et al, Key of Diagnosis and Treatment for Depressive Disorder, Phoenix Science Press, 2003, p 2-3).

The pathogenesis of depression is very complex, and the occurrence of depression may relate to nerve functional unbalance of monoamine-type neurotransmitters in brain. The hypotheses of noradrenalin and 5-hydroxytryptamine are widely applied to the biological pathogenesis of depression (J I Jianlin et al, Analysis of Somatic Symptoms of Depression and Relative Factors, Chinese Mental Health Journal, 2002, 16(9):605-608).

At present, depression is treated with medication, psychotherapy, electroshock therapy and the like, and medication is still the primary means. The long-term administration of the western medicine—antidepressant may result in adverse reactions in nerve system, anticholinergic, cardiovascular aspects. Although novel antidepressants (e.g. SSRI, NaSSA, SNRI and the like) have better safety and tolerance, many patients cannot afford the treatment, especially the long-term treatment due to their higher price, so that the patients' compliance is decreased and the treatment is affected.

The treatment of emotional diseases with traditional Chinese medicine has a history of about 2000 years. The clinical manifestations of depression indicate that the disease may be categorized into Syndrome of Melancholia (Yu zheng), Hysteria (Zangzao), Lily Disease (Baihebing), Insomnia and the like in traditional Chinese medicine. The diagnosis and treatment of this disease should follow the same for "Syndrome of Melancholia (Yuzheng)" in traditional Chinese medicine. In recent years, some traditional Chinese medical formulae are applied in the treatment of depression and proved to have good therapeutic effects. Moreover, many studies demonstrate that the traditional Chinese medicinal formulation may improve the behaviors of animal models for depression and be favorable to the central nerve transmitters. Under the concept of wholism, treatment of depression with traditional Chinese medicine is based on overall analysis of symptoms and signs, the cause, nature and location of the illness and the patient's physical condition according to the basic theories of traditional Chinese medicine, which has definite and sustainable therapeutic effects, safety, and better patient's compliance, especially is adaptable to patients suffering from minor or moderate depression with the adjustment of life styles. The traditional Chinese medicine is safe, effective and economical, which also satisfies the requirements for therapeutic effect on patients suffering from depression. (YANG Shiyou et al, Effects of Jie Bai You Oral liquor on Behaviours of Rat Models for Depression and the Central Nerve Transmitters, Chinese Journal of Basic Medicine in Traditional Chinese Medicine, 2000, 6(11):56-59).

According to the theory of traditional Chinese medicine and Zhang Zhong-jing's (a famous doctor in Eastern Han Dynasty of China) academic ideology on the treatment of emotional diseases, the inventor profoundly studies how emotions lead to depression, and emphasizes the fact that such emotional factors as depression, gloominess, sadness or over-worry will lead to liver failing to maintain the normal flow of Qi, dysfunction of the spleen in transport and heart-spirit support loss, so as to render multi-entrails functional disorder. The inventor also points out that stagnation of liver-Qi leads to stagnant-fire, which influences to the body fluid and further leads to sputum, thus results in the pathogenesis of Qi stagnation, sputum accumulation, and fire disturbance. With clinical experiences of medication for the treatment of mental and neurological diseases, the inventor contrives a traditional Chinese medicinal composition to effectively alleviate of mental depression and relieve restlessness, and provides a novel traditional Chinese medicine formulation of the present invention, which has excellent therapeutic effects and is safe for patients suffering from depression. Up to now, there is no report relevant to the traditional Chinese medicinal composition of the present invention and the formulation thereof.

CONTENTS OF THE INVENTION

The object of the present invention is to provide a traditional Chinese medicinal composition for treating depression, which has a notable therapeutic effect.

Another object of the present invention is to provide a method for preparing the traditional Chinese medicinal composition.

A third object of the present invention is to provide a traditional Chinese medicinal mixture prepared according to the method for preparing the traditional Chinese medicinal composition.

A fourth object of the present invention is to provide a pharmaceutical formulation containing the traditional Chinese medicinal mixture or the traditional Chinese medicinal composition of the present invention.

A fifth object of the present invention is to provide a method for preparing the pharmaceutical formulation of the present invention.

A sixth object of the present invention is to provide the use of the traditional Chinese medicinal composition in the manufacture of a medicament for treating depression.

The traditional Chinese medicinal composition of the present invention comprises, as active components, the traditional Chinese medicinal materials Fructus Gardeniae, Fructus Forsythiae, Rhizoma Pinelliae and Cortex Magnoliae Officinalis for treating minor and moderate depression with characteristics of Syndrome of Stagnation of Qi and Accumulation of Phlegm, Internal Disturbance of Stagnated Fire and the symptoms include low spirits, sentimental, annoyed, restlessness, insomnia, trance, etc., and the somatic symptoms include oppressed feeling in chest, pharyngeal trouble, liable to sighing, anorexia, abdominal distention, constipation, etc.

The traditional Chinese medicinal composition of the present invention consists of the traditional Chinese medicinal materials: 120-200 parts by weight of Fructus Gardeniae, 300-500 parts by weight of Fructus Forsythiae, 120-200 parts by weight of Cortex Magnoliae Officinalis and 180-300 parts by weight of Rhizoma Pinelliae.

Preferably, the traditional Chinese medicinal composition of the present invention comprises the active components (based on the traditional Chinese medicinal materials): 135-185 parts by weight of Fructus Gardeniae, 310-490 parts by weight of Fructus Forsythiae, 130-180 parts by weight of Cortex Magnoliae Officinalis and 200-280 parts by weight of Rhizoma Pinelliae, more preferably 148-172 parts by weight of Fructus Gardeniae, 380-430 parts by weight of Fructus Forsythiae, 138-175 parts by weight of Cortex Magnoliae Officinalis and 220-260 parts by weight of Rhizoma Pinelliae.

In order to achieve better therapeutic effects, the traditional Chinese medicinal composition of the present invention further comprises Caulis Perillae, Fructus Aurantii and Poria as active components, based on weight 144-240 parts for Caulis Perillae, 120-200 parts for Fructus Aurantii and 144-240 parts for Poria.

In order to achieve optimal therapeutic effects, the traditional Chinese medicinal composition of the present invention may further comprise Radix Glycyrrhizae as active components, 36-60 parts by weight of Radix Glycyrrhizae. The preferred composition includes Fructus Gardeniae as the principal drug, Fructus Forsythiae, Cortex Magnoliae Officinalis and Rhizoma Pinelliae as the ministerial drugs, Caulis Perillae, Fructus Aurantii and Poria as the adjunctive drugs, and Radix Glycyrrhizae as the conductant drug. The combination of said components can reduce stagnated heat, promote Qi flow, eliminate accumulated sputum, regulate the function of Zang-fu, and can make mind peaceful. Attention is given to appearance and substance so as to achieve the efficacy of reducing stagnated heat, removing restlessness, promoting Qi and eliminating sputum.

Preferably, the traditional Chinese medicinal composition of the present invention comprises the active components below (based on the traditional Chinese medicinal materials) 120-200 parts by weight of Fructus Gardeniae, 300-500 parts by weight of Fructus Forsythiae, 120-200 parts by weight of Cortex Magnoliae Officinalis, 180-300 parts by weight of Rhizoma Pinelliae, 120-200 parts by weight of Fructus Aurantii, 144-240 parts by weight of Poria, 144-240 parts by weight of Caulis Perillae, and 36-60 parts by weight of Radix Glycyrrhizae.

Preferably, the traditional Chinese medicinal composition of the present invention comprises the active components below (based on the traditional Chinese medicinal materials) 135-185 parts by weight of Fructus Gardeniae, 310-490 parts by weight of Fructus Forsythiae, 130-180 parts by weight of Cortex Magnoliae Officinalis, 200-280 parts by weight of Rhizoma Pinelliae, 140-190 parts by weight of Fructus Aurantii, 164-230 parts by weight of Poria, 154-230 parts by weight of Caulis Perillae, and 38-58 parts by weight of Radix Glycyrrhizae.

Preferably, the traditional Chinese medicinal composition of the present invention comprises the active components below (based on the traditional Chinese medicinal materials) 148-172 parts by weight of Fructus Gardeniae, 380-430 parts by weight of Fructus Forsythiae, 138-175 parts by weight of Cortex Magnoliae Officinalis, 220-260 parts by weight of Rhizoma Pinelliae, 149-175 parts by weight of Fructus Aurantii, 176-220 parts by weight of Poria, 184-220 parts by weight of Caulis Perillae, and 40-55 parts by weight of Radix Glycyrrhizae.

Preferably, the traditional Chinese medicinal composition of the present invention comprises the active components below (based on the traditional Chinese medicinal materials) 120 parts by weight of Fructus Gardeniae, 300 parts by weight of Fructus Forsythiae, 200 parts by weight of Cortex Magnoliae Officinalis, 280 parts by weight of Rhizoma Pinelliae, 190 parts by weight of Fructus Aurantii, 240 parts by weight of Poria, 180 parts by weight of Caulis Perillae, and 55 parts by weight of Radix Glycyrrhizae.

Preferably, the traditional Chinese medicinal composition of the present invention comprises the active components below (based on the traditional Chinese medicinal materials) 200 parts by weight of Fructus Gardeniae, 300 parts by weight of Fructus Forsythiae, 120 parts by weight of Cortex Magnoliae Officinalis, 200 parts by weight of Rhizoma Pinelliae, 120 parts by weight of Fructus Aurantii, 150 parts by weight of Poria, 240 parts by weight of Caulis Perillae, and 40 parts by weight of Radix Glycyrrhizae.

Preferably, the traditional Chinese medicinal composition of the present invention comprises the active components below (based on the traditional Chinese medicinal materials) 160 parts by weight of Fructus Gardeniae, 400 parts by weight of Fructus Forsythiae, 160 parts by weight of Cortex Magnoliae Officinalis, 240 parts by weight of Rhizoma Pinelliae, 160 parts by weight of Fructus Aurantii, 192 parts by weight of Poria, 192 parts by weight of Caulis Perillae, and 48 parts by weight of Radix Glycyrrhizae.

Preferably, the traditional Chinese medicinal composition of the present invention comprises the active components below (based on the traditional Chinese medicinal materials) 160 parts by weight of Fructus Gardeniae, 480 parts by weight of Fructus Forsythiae, 150 parts by weight of Cortex Magnoliae Officinalis, 210 parts by weight of Rhizoma Pinelliae, 160 parts by weight of Fructus Aurantii, 200 parts by weight of Poria, 240 parts by weight of Caulis Perillae, and 60 parts by weight of Radix Glycyrrhizae.

Cortex Magnoliae Officinalis and Rhizoma Pinelliae of the present invention can be replaced by stir-baked Cortex Magnoliae Officinalis with rhizoma zingiberis recens juice and prepared Rhizoma Pinelliae with juice of rhizoma zingiberis recens respectively.

As seen from the clinical manifestations, depression may be categorized Syndrome of Melancholia (Yuzheng), Hysteria (Zangzao), Lily Disease (Baihebing), Insomnia and the like in traditional Chinese medicine. It is characterized as Syndrome of Stagnation of Qi and Accumulation of Phlegm, Internal Disturbance of Stagnated Fire, and has one or more mental symptoms selected from low spirits, sentimental, annoyed, restlessness, insomnia and trance, etc., and somatic symptoms selected from oppressed feeling in chest, pharyngeal trouble, liable to sighing, anorexia, abdominal distension and constipation, etc. According to "Syndrome of Stagnation of Qi (Yuzheng)" in traditional Chinese medicine, this syndrome should be determined and treated based on pathogenesis obtained through differentiation of symptoms and signs. Severe life events and environment-stressful events are the depression-inducing factors. Due to a hurt to emotions, such as depression, gloominess, sadness or over-worry, etc., liver fails to maintain the normal flow of Qi, and dysfunction of the spleen in transport and heart-spirit support loss are rendered, so as to render a disorder of entrails, Yin and Yang, Qi and blood, which has close relations with liver, heart and spleen.

Liver has the function of smoothing and regulating flow of Qi and Blood, and prefers free activity in nature. If the function of liver is normal, Qi and blood will be mild and the spirit will be cheerful. If emotional disorder occurs, liver fails to maintain the normal flow of Qi, and the functional activity of Qi is not smooth, so as to render stagnation of liver-Qi, which appears to be mental depression, oppressed feeling in chest and liable to sighing. Spleen has the function of transporting and transforming nutrients, and thinking and ideas are related to the spleen. If liver may not sufficiently smooth and regulate flow of Qi and Blood, it fails to dredge the spleen; if transverse invasion of hyperactiver liver-Qi occurs, liver has hyperfunction, which may affect the functioning of spleen, so as to result in dysfunction of the spleen in transport, anorexia, abdominal distention and constipation. If there lacks source of generating Qi and blood, or there is over-worry, heart-spirit losses support, which appears to be loss of spirit, low spirits, palpitation and insomnia and susceptible to fright and fear. If Qi flows freely, then the body fluid is promoted to circulation; if Qi flows freely then emotional depression may be relieved. Stagnation of Qi renders the body fluid to accumulate to phlegm; if phlegm and Qi are accumulated in the throat, globus hystericus will be caused. If phlegm confuses the mind, mental activity is inhibited so as to result in trance, hypomnesia and attention deficit disorder. Fire-syndrome resulting from stasis and heat trouble will render upsetting. The heart takes charge of mental activities. Dysfunction of mental activities will result in sentimental, annoyed and restlessness.

The primary task of the traditional Chinese medicinal composition of the present invention is to relieve restlessness and alleviate depression. On the basis of bitter, acrid, cool, moist, and unobstructed conditions, the therapeutic principles of clearing hot, removing restlessness, promoting Qi and eliminating sputum are applied. Lysis of accumulative heat in chest and diaphragm will relieve restlessness; and the regulation of Qi and the dredging of stasis will relieve the sensation of fullness, so as to achieve peaceful mind and normal mental activities. Said composition not only can relieve somatic symptoms of patients, but also can alleviate harmful feelings of patients, such as anxiety, depression and the like.

According to the modern medical theories, the depression in the present invention refers to a class of mental disorders or emotional disorders comprising not only unipolar depression attack (endogenous depression disorder) and bipolar disorder depression attack conventionally categorized into emotional disorders, but also dysthymia (also called neurotic depression), psychogenic depressive disorders, depressive disorders accompanied with brain or somatic diseases, anxiety, depression accompanied with psychoactive substance-induced mental disorders or non-addictive substance-induced mental disorders, postpsychotic depression and the like.

The traditional Chinese medicinal materials, as active components, in the traditional Chinese medicinal composition of the present invention are described as follows (wherein Latin names and the processing methods are stemmed from *Grand Dictionary of Chinese Traditional Medicine,* 1977-7, 1$^{St}$ Edition, Shanghai Science & Technology Press, and Chinese *Pharmacopoeia,* 2005, Chemical Industry Press).

Fructus Gardeniae in the present invention is dry and mature fruits of *Gardenia jasminoides* Ellis (or *Gardenia florida* L.). Fruits are harvested in September to November when they mature and present reddish yellow. After fruit stalks and impurities are removed, fruits thereof are steamed or passed through boiling water, taken out and dried.

Fructus Forsythiae in the present invention is dry fruits of *Forsythia suspensa* (Thunb.) Vahl. Fruits are harvested when they initially mature and are still green in autumn. After impurities are removed, said fruits are steamed and dried, which produces the "green Fructus Forsythiae". When said fruits completely mature, they are harvested and dried. Then impurities therein are removed to obtain the often called "old Fructus Forsythiae". The type used in the present invention is green Fructus Forsythiae.

Fructus Aurantii in the present invention is dried and immature fruits of *Citrus aurantium* L., *Poncirus trifoliate* (L.) Raf, *Citrus wilsonii* Tanaka, *Citrus aurantium* L. var *amara* Engl., *Citrus sinensis* (L.) Osbeck, or *Citrus medica* L. and their variants cultured. Fructus Aurantii is harvested when the pericarp thereof is still green in July. It is transversely cut from the middle into two halves, dried in sunlight or dried in low temperature.

Cortex Magnoliae Officinalis in the present invention is dried bark, root bark and branch bark of *Magnolia officinalis* Rehd. et Wils. or *Magnolia officinalis* Reha. et Wils. *biloba* Rehd. et Wils. Root bark and branch bark are peeled off from April to June and directly dried in the shade. Dried bark is slightly steamed in boiling water and stacked in dank places for "diaphoresis" and the diaphoresis is conducted to the extent that the endocuticle becomes purple brown or chocolate brown. Then said bark is steamed soft, taken out, rolled into a tubular shape and dried.

Processing method for the preparation of the stir-baked Cortex Magnoliae Officinalis with rhizoma zingiberis recens juice: the stir-baked Cortex Magnoliae Officinalis with rhizoma zingiberis recens juice is Cortex Magnoliae Officinalis threads, and Cortex Magnoliae Officinalis threads are stir-fried according to the stir-frying method with ginger juice (when stir-baking with ginger juice is used, fresh ginger should be firstly cleaned, mashed, then a suitable amount of water is added, and the fresh ginger is squeezed to obtain the juice. The ginger dregs are squeezed again after another suitable amount of water is added. The juice obtained twice is combined together to form "ginger juice". If rhizoma zingiberis is used, it is mashed and decocted twice with water. The decoctions obtained are combined and filtrated to obtain a filtrate as ginger juice. The clean medicinal materials are homogeneously mixed with ginger juice, placed in a kettle and stir-fried to the extent that ginger juice is completely adsorbed, or taken out and dried when reaching the prescribed extent. Except regulation to the contrary, 10 kg fresh ginger or 3 kg rhizoma zingiberis are used for per 100 kg clean medicinal material).

Rhizoma Pinelliae in the present invention is dry rhizome of Pinellia ternate (Thunb.) Breit., Typhonium flagelliforme (Lodd.) or Pinellia pedatisecta Schott.

Processing method for the preparation of the prepared Rhizoma Pinelliae with juice of rhizoma zingiberis recens: the clean Rhizoma Pinelliae are steeped in boiling water to the extent that there are no dry cores after large Rhizoma Pinelliae is separated from small Rhizoma Pinelliae. Fresh ginger is cut into slices and decocted. Alum is added and completely decocted with Rhizoma Pinelliae. Rhizoma Pipelliae is then taken out, dried to damp dry, cut into slices and dried.

Poria in the present invention is dry sclerotium of Poria cocos (Schw.) Wolf, Poria Cum Ligno Hospite (FU Shen) (dry fungus of Poria cocos (Schw.) Wolf embraces the white portion of masson pine root), skin of Poria (dry sclerotium husk of Poria cocos (Schw.) Wolf), or Poria hostwood (Fu Shen Mu) (masson pine root embraced in the middle of dry fungus of Poria cocos (Schw.) Wolf). Generally, Poria is dug out from July to September. After earth and sand are removed, Poria is stacked for "diaphoresis", laid open to dry to the extent of surface dried. Then diaphoresis is done again. After the aforesaid steps are repeated several times to the extent that wrinkles show and most of the endogenous water is dissipated, Poria is dried in the shade to obtain Poria pieces, or fresh Poria is cut by different parts and dried in the shade to obtain "Poria exodermis" and "clump" respectively.

Caulis Perillae in the present invention is dry stalk of Perilla frutescens (L.) Britt., Perilla frutescens (L.) Britt. var. crispa (Thunb.) Hand.-Mazz., or Perilla frutescens (L.) Britt. var. acuta (Thunb.) Kudo. The stalks are mown in autumn when the fruits mature. Impurities are removed, and the stalks are dried; or fresh stalks are cut into slices and dried.

Radix Glycyrrhizae in the present invention is dry root and rhizome of Glycyrrhiza uralensis Fisch., Glycyrrhiza inflata Bat., or Glycyrrhiza Glabra L. Radix Glycyrrhizae is dug in spring and autumn and dried after fibrous roots thereof are removed.

The traditional Chinese medicinal composition of the present invention can be prepared by pulverizing the active components—traditional Chinese medicinal materials into fine powder and homogeneously mixing the powder.

The traditional Chinese medicinal composition of the present invention can also be orally administered by decocting the traditional Chinese medicinal materials as active components with water according to the traditional method of decocting the traditional Chinese medicine, concentrating the decoction to obtain a water decoctum.

In order to sufficiently exert the efficacy of each active components in the traditional Chinese medicinal composition of the present invention, traditional Chinese medicinal materials including Fructus Gardeniae, Fructus Aurantii, Cortex Magnoliae Officinalis and Fructus Forsythiae are preferably extracted with ethanol; and Poria, Caulis Perillae and Radix Glycyrrhizae are extracted preferably by decoction with water.

The traditional Chinese medicinal composition of the present invention is preferably prepared according to the following method comprising the following steps:
1) weighing Fructus Gardeniae, Cortex Magnoliae Officinalis and Fructus Forsythiae by said parts, and crushing Fructus Gardeniae, mixing these traditional Chinese medicinal materials, and extracting the mixture 1-3 times with 6-10 times amount of 50-80% ethanol for 1-3 h each time, filtering the extracts, combining the filtrates together and concentrating the filtrates to obtain a clear mastic having a relative density (which represents the density relative to water in the present invention) of 1.01-1.04 and then having it in stock;
2) weighing Rhizoma Pinelliae by said parts, crushing and grinding it into fine powder and having it in stock; and
3) mixing the Rhizoma Pinelliae powder with the clear mastic obtained from step 1) to obtain the active ingredients of the traditional Chinese medicinal composition of the present invention.

Further, the traditional Chinese medicinal composition of the present invention is prepared preferably according to the following method comprising the following steps:
1) weighing Fructus Gardeniae, Fructus Aurantii, Cortex Magnoliae Officinalis and Fructus Forsythiae by said parts, and crushing Fructus Gardeniae, mixing these traditional Chinese medicinal materials and extracting the mixture 1-3 times with 6-10 times amount of 50-80% ethanol for 1-3 hours each time, filtering the extracts, combining the filtrates together and concentrating the filtrates to obtain a clear mastic having a relative density of 1.01-1.04 and then having it in stock;
2) weighing Poria, Caulis Perillae and Radix Glycyrrhizae by said parts, decocting them for three times (one to three hours for each time) with 8-10 times amount of water for the first time and respectively 6-8 times amount of water for the second and third time, combining the extracts, and concentrating them to obtain a clear mastic having a relative density of 1.10-1.15 and having it in stock;
3) weighing Rhizoma Pinelliae by said parts, pulverizing and screening it with a screen having 80-100 meshes and having the powder obtained in stock; and
4) mixing the Rhizoma Pinelliae powder obtained from step 3) with the clear mastics obtained from steps 1) and 2), the mixture obtained is dried, and pulverized into powders to obtain the active ingredients of the traditional Chinese medicinal composition of the present invention.

The traditional Chinese medicinal composition of the present invention can be prepared into any conventional formulations according to the conventional method for preparing a traditional Chinese medicinal formulation. For example, the traditional Chinese medicinal materials as active components are pulverized into fine powders and homogeneously mixed to form a powder. In addition, the traditional Chinese medicinal composition of the present invention can be prepared according to the conventional processes for preparing formulations, e.g. the preparation processes disclosed in *Chinese Medicine Pharmacy*, FAN Biting, Shanghai Science & Technology Press, 1997-12, $1^{st}$ Edition, into any pharmaceutically acceptable conventional dosage forms, such as capsules, tablets, pills, oral liquor, soft capsules, drop pills and the like.

The formulation of the present application may comprises any optional conventional adjuvants in the formulation field, such as fillers, disintegrating agents, binders, flow aids, antioxidants, flavoring agents, sweeting agents, suspending agents and the like. Said adjuvants include, for example, starch, sucrose, lactose, dextrin, amylum pregelatinisatum, crosslinked polyvinylpyrrolidone and the like, or any other Chinese medicine-pharmaceutically acceptable adjuvants (see the adjuvants disclosed in various dosage forms in *Chinese Medicine Pharmacy*, FAN Biting, Shanghai Science & Technology Press, 1997-12, $1^{st}$ Edition,)

The traditional Chinese medicinal formulation of the present invention is prepared preferably according to the following method comprising the following steps:
1) weighing Fructus Gardeniae, Fructus Aurantii, Cortex Magnoliae Officinalis and Fructus Forsythiae by said partss, and crushing Fructus Gardeniae, mixing these traditional Chinese medicinal materials and extracting the mixture 1-3 times (one to three hours for each time) with 6-10 times amount of 50-80% ethanol, filtering the extracts, combining the filtrates together and concentrating the filtrates to obtain a clear mastic having a relative density of 1.01-1.04 and then having it in stock;
2) weighing Poria, Caulis Perillae and Radix Glycyrrhizae by said partss, decocting them for three times (one to three hours for each time) with 8-10 times amount of water for the first time and respectively 6-8 times amount of water for the second and third times, combining the decoctions, and concentrating them to obtain a clear mastic having a relative density of 1.10-1.15 and having it in stock;
3) weighing Rhizoma Pinelliae by said parts, pulverizing and screening it with a screen having 80-100 meshes and having the powder obtained in stock;
4) feeding the Rhizoma Pinelliae powder obtained from step 3) into the material can of the spray-drying granulating machine, introducing hot air into the can, spraying to the can the clear mastics obtained from steps 1) and 2) after the Rhizoma Pinelliae powder and a suitable amount of any optional adjuvants are preheated and dried, homogeneously mixing, drying to granulation, to obtain the active ingredients of the pharmaceutical formulation of the present invention.

The active ingredient particles obtained in step 4) and a suitable amount of any optional adjuvants are screened with a screen having 18 meshes and granulating them, and then filling the particles obtained into gelatine capsules to obtain the capsule of the present invention.

The active ingredient particles prepared in step 4) are mixed with a suitable amount of any optional adjuvants according to the conventional method for preparing tablets, and the mixture is compressed into tablets.

The clear mastics obtained from steps 1) and 2) are mixed with the Rhizoma Pinelliae powder obtained from step 3), and a suitable amount of adjuvants are added to form a pill, an oral suspension, a soft capsule or a drop pill according to the conventional methods for the preparation of formulations (the preparation processes disclosed in *Chinese Medicine Pharmacy*, FAN Biting, Shanghai Science & Technology Press, 1997-12, 1$^{st}$ Edition).

In the preparation methods above, dry granulation is preferably spraying granulation. The spray-drying granulating machine preferably has the parameters of a frequency conversion rate of 6-12 Hz, a temperature of 70-80□ in the main air blower and a total compressed air pressure of 0.4 MPa.

Based on the total weight of the active components, traditional Chinese medicinal materials, the traditional Chinese medicinal composition of the present invention is administered in an amount of 10-30 g per day, and may be administered once per day, preferably 2-4 times per day.

EXAMPLES

The following examples are used to illustrate the preparation of the formulations of the traditional Chinese medicinal composition of the present invention, a capsule, a tablet, a pill and an oral liquor, but do not limit the scope of the present invention.

The traditional Chinese medicinal materials used in the examples, including Fructus Gardeniae, Fructus Forsythiae, stir-baked Cortex Magnoliae Officinalis with rhizoma zingiberis recens juice, prepared Rhizoma Pinelliae with juice of rhizoma zingiberis recens, Fructus Aurantii, Poria, Caulis Perillae, Radix Glycyrrhizae and adjuvants, all were purchased from Anguo Chinese Herbal Medicine Material Co., Ltd (Batch No. Fructus Gardeniae (20010502), Fructus Forsythiae (20010611), stir-baked Cortex Magnoliae Officinalis with rhizoma zingiberis recens juice (20010522), prepared Rhizoma Pinelliae with juice of rhizoma zingiberis recens (20010426), Fructus Aurantii (20010518), Poria (20010518), Caulis Perillae (20010521), Radix Glycyrrhizae (20010516), starch (20010327), crosslinked polyvinylpyrrolidone (20010619), lactose (20010209), polyvinylpyrrolidone (20010616) and magnesium stearate (20010528)).

Example 1

Preparation of Capsules of the Present Invention

Recipe:
160 g Fructus Gardeniae, 400 g Fructus Forsythiae, 160 g stir-baked Cortex Magnoliae Officinalis with rhizoma zingiberis recens juice, 240 g prepared Rhizoma Pinelliae with juice of rhizoma zingiberis recens, 160 g Fructus Aurantii, 192 g Poria, 192 g Caulis Perillae, and 48 g Radix Glycyrrhizae Preparation Method:
1) weighing clean Fructus Gardeniae, Fructus Aurantii, stir-baked Cortex Magnoliae Officinalis with rhizoma zingiberis recens juice and Fructus Forsythiae according to the recipe, and crushing Fructus Gardeniae, mixing these traditional Chinese medicinal materials, and extracting the mixture 2 times (2 hours for each time) with 8 times amount of 60% (v/v) ethanol, filtering the extracts, concentrating the filtrate to obtain a clear mastic having a relative density of 1.01-1.04 for each time and combining said clear mastics and then having them in stock;
2) weighing Poria, Caulis Perillae and Radix Glycyrrhizae according to the recipe, decocting them for three times (2 hours for each time) with 9 times amount of water for the first time and respectively 7 times amount of water for the second and third time, combining the decoctions, and concentrating them to obtain a clear mastic having a relative density of 1.10-1.15 and having it in stock;
3) weighing prepared Rhizoma Pinelliae with juice of rhizoma zingiberis recens according to the recipe, pulverizing and screening it with a screen having 80 meshes and having the powders obtained in stock;
4) combining the clear mastics obtained from steps 1) and 2), feeding the Rhizoma Pinelliae powder and 50 g starch (filler) into the material can of the spray-drying granulating machine, introducing hot air, spraying to the can the combined clear mastics after the Rhizoma Pinelliae powder and starch are preheated and dried, spray-drying for granulation (with a frequency conversion rate of 6-12 Hz, a temperature of 70-80□ in the main air blower and a total compressed air pressure of 0.4 MPa); and
5) screening the particles obtained from step 4) with a screen having 18 meshes, and encapsulating the particles to obtain 1000 capsules.

Example 2

Preparation of Tablets of the Present Invention

Recipe:
120 g Fructus Gardeniae, 300 g Fructus Forsythiae, 200 g Cortex Magnoliae Officinalis, 280 g Rhizoma Pinelliae, 190 g Fructus Aurantii, 240 g Poria, 180 g Caulis Perillae, and 55 g Radix Glycyrrhizae Preparation Method:
Preparing clear mastics according to the methods as stated in step 1) and 2) of Example 1, combining the clear mastics, feeding the Rhizoma Pinelliae powder prepared according to the method as stated in step 3) of Example 1 and 20 g lactose into the material can of the spray-drying granulating machine, introducing hot air, spraying to the can the combined clear mastics after the Rhizoma Pinelliae powder and lactose are preheated and dried, spray-drying for granulation (with a frequency conversion rate of 6-12 Hz, a temperature of 70-80□ in the main air blower and a total compressed air pressure of 0.4 MPa), weighing the particles obtained, adding 1% magnesium stearate as a lubricant and compressing them into 1000 tablets.

Example 3

Preparation of Pills of the Present Invention

Recipe:
200 g Fructus Gardeniae, 300 g Fructus Forsythiae, 120 g stir-baked Cortex Magnoliae Officinalis with rhizoma zingiberis recens juice, 200 g prepared Rhizoma Pinelliae with juice of rhizoma zingiberis recens, 120 g Fructus Aurantii, 150 g Poria, 240 g Caulis Perillae, and 40 g Radix Glycyrrhizae Preparation Method:

Preparing clear mastics according to the methods as stated in step 1) and 2) of Example 1, homogeneously mixing the clear mastics with the Rhizoma Pinelliae powder prepared according to the method as stated in step 3) of Example 1, properly drying the mixture by baking, forming pill strip, slicing and rubbing it into 1000 pills.

Example 4

Preparation of Oral Suspension of the Present Invention

Recipe:
160 g Fructus Gardenia; 480 g Fructus Forsythiae, 150 g Cortex Magnoliae Officinalis, 210 g Rhizoma Pinelliae, 160 g Fructus Aurantii, 200 g Poria, 240 g Caulis Perillae, and 60 g Radix Glycyrrhizae Preparation Method:

Preparing clear mastics according to the methods as stated in step 1) and 2) of Example 1, homogeneously mixing the clear mastics with the Rhizoma Pinelliae powder prepared according to the method as stated in step 3) of Example 1; weighing 5 g ethyl hydroxy benzoate and dissolving with 10 ml ethanol as an antiseptic, adding the solution to the above mixture, adding the mixture obtained 300 g polyvinylpyrrolidone as a suspending agent, then adding it purified water to 10,000 ml, stirring and homogeneously mixing the suspension, filling it into bottles and sealing to obtain 1000 oral suspensions.

Example 5

Preparation of Soft Capsules of the Present Invention

Recipe:
200 g Fructus Gardeniae, 500 g Fructus Forsythiae, 192 g Cortex Magnoliae Officinalis, 180 g Rhizoma Pinelliae, 160 g Fructus Aurantii, 144 g Poria, 144 g Caulis Perillae, and 36 g Radix Glycyrrhizae Preparation Method:

Preparing clear mastics according to the methods as stated in step 1) and 2) of Example 1, homogeneously mixing the clear mastics with the Rhizoma Pinelliae powder prepared according to the method as stated in step 3) of Example 1, adding to the mixture 10 g silicon dioxide as an adsorbent, sodium dodecyl sulfate as an emulsifier and 100 g vegetable oil as a solvent, sufficiently stirring and homogeneously mixing it, and sealing the mixture obtained to obtain 1000 soft capsules.

Example 6

Preparation of Tablets of the Present Invention

Recipe:
160 g Fructus Gardeniae, 400 g Fructus Forsythiae, 160 g stir-baked Cortex Magnoliae Officinalis with rhizoma zingiberis recens juice, and 240 g prepared Rhizoma Pinelliae with juice of rhizoma zingiberis recens Preparation Method:

1) weighing clean Fructus Gardeniae, stir-baked Cortex Magnoliae Officinalis with rhizoma zingiberis recens juice and Fructus Forsythiae according to the recipe, and crushing Fructus Gardeniae, mixing these traditional Chinese medicinal materials, and extracting the mixture 2 times (2 hours each time) with 8 times amount of 60% ethanol and, filtering the extracts, concentrating the filtrate to obtain a clear mastic having a relative density of 1.01-1.04 each time and combining said clear mastics and having them in stock;

2) weighing prepared Rhizoma Pinelliae with juice of rhizoma zingiberis recens according to the recipe, pulverizing and screening it with a screen having 80 meshes and having the powders obtained in stock;

3) feeding the Rhizoma Pinelliae powder and 80 g amylum pregelatinisatum into the material can of the spray-drying granulating machine, introducing into the can hot air, and spraying to the can the clear mastic obtained in step 1) after the Rhizoma Pinelliae powder and amylum pregelatinisatum are preheated and dried, spray-drying for granulation (with a frequency conversion rate of 6-12 Hz, a temperature of 70-80□ in the main air blower and a total compressed air pressure of 0.4 MPa); and 4) screening the particles obtained from step 3) with a screen having 18 meshes, weighing the particles obtained, adding to them 1% magnesium stearate and compressing them into 1000 tablets.

Example 7

Preparation of Tablets of the Present Invention

Recipe:
120 g Fructus Gardeniae, 300 g Fructus Forsythiae, 200 g Cortex Magnoliae Officinalis, and 280 g Rhizoma Pinelliae, Preparation Method:

weighing clean Fructus Gardeniae, Fructus Forsythiae, Cortex Magnoliae Officinalis and Rhizoma Pinelliae according to the recipe, pulverizing these traditional Chinese medicinal materials, adding to them 150 g lactose and homogeneously mixing them, adding to the mixture a suitable amount of 0.5% polyvinylpyrrolidone as a binder to prepare proper soft materials, granulating them, drying the particles obtained by baking, screening with a screen having 18 meshes and weighing the particles, adding to them 1% magnesium stearate and compressing them into 1000 tablets.

Pharmacological Activity Tests for the Traditional Chinese Medicinal Composition of the Present Invention In order to demonstrate the activity of alleviating depression and relieving restlessness presented in the traditional Chinese medicinal composition of the present invention, the following animal tests are carried out by using the capsules prepared according to the method in Example 1 above (hereinafter referred to as the capsules of the present invention) to verify the therapeutic effects thereof.

The primary pharmacodynamic tests are performed on the basis of the capsules of the present invention to testify the effectiveness of the present invention.

Test Materials

1. Drugs to be tested: the powder from the capsule prepared in Example 1 of the present invention, light yellow powder, 3.88 g crude drug (the traditional Chinese medicinal material)/1 g powder, batch No. 2004226, provided by Shijiazhuang Yiling Pharmaceutical Co., Ltd. Before administration, said powder is diluted with double distilled water to achieve a required concentration.

2. Animals: ICR male mouse (grade: SPF/VAF) purchased from Beijing Vital River Experimental animal Technical Co., Ltd, License No. SCXK (JING) 2002-2003.

3. Breeding environment: The animals are bred in the barrier environment of China Academy of Chinese Medical Sciences Medical Experimental Animal Center, License No. SYXK (JING) 2000-0048. Feedstuffs are provided by The Academy of Military Medical Sciences, License No. SCXK (JUN) 2002-0018

4. Drugs and Reagents

Amitriptyline Hydrochloride Tablets, 25 mg per tablet, provided by Changzhou Siyao Pharmaceuticals Co., Ltd., batch No. 9906222;

Fluose fine hydrochloride (Fluoxetine Hydrochloride dispersible tablets), 20 mg per tablet, produced by Eli Lilly and Company, batch No. A042635;

Reserpine injection, 1 mg/ml, Shanghai Fudan Forward Pharmaceutical Co., Ltd, batch No. 030206;

Aspirin enteric-coated tablets, 40 mg per tablet, Beijing Shuguang Pharmaceutical Industrial Co., Ltd, batch No. 050123;

Sodium pentobarbital, FW248.26, Beijing Chemical Reagents Company, imported from Germany and subpackaged, batch No. 020402;

L-Norepinephrine.bitartrate, FW337.3, a product from SERVA;

Serotonin creatinine sulfate, FW 405.43, a product from Fluka;

Dopamine hydrochloride, FW189.64, having a purity higher than 98.5%;

5-Hydroxyindole-3-acetic acid, 5-HIAA, FW 191.2, from Sigma;

o-Phthalaldehyde, from China Wulian Chemical Plant, chemically pure, batch No. 960117;

n-Butanol, AR molecular weight of 74.12, produced by Beijing Chemical Factory, batch No. 960409; and n-Heptane, AR molecular weight of 100.21, produced by Beijing Chemical Factory, batch No. 940121.

Pargyline hydrochloride, 1 g per bottle, FW195.7, from Sigma.

Other reagents are analytically pure and purchased from Beijing Chemical Reagents Company.

5. Apparatus

Quadriconducts electrophysiologyraph RM6240C type physiological experiment system, manufactured by Chengdu Instrument Factory;

Muscle tonus energy transducer, JZ100 type, manufactured by Gaobeidian Xinhang Machinery & Electrical Equipment Co., Ltd.

Fluorescence spectrophotometer, HITACHI 650-60type, produced by HITACHI, Japan;

Spontaneous activity recorder, OPTO-VARIMEX-3 type, produced by Columbus Instruments, Japan;

Automated glass homogenizer, DY-89-1 type, produced by Ningbo Xinguang Scientific Instrument Institute;

Semi-Automatic Biochemical Analyser, manufactured by Beijing Zhongsheng Instrument Factory;

Aqueous thermostat, manufactured by Shanghai Medical Instruments Co., Ltd Medical Instruments Factory No. 5;

Precision balance, SARTORIUS BP110S type, manufactured by SARTORIUS, Germany;

High speed centrifuge, SORVALL SUPER-T21 type, manufactured by SORVALL, USA;

Digital Thermometer, WMY-01 type, manufactured by Shanghai Huachen Medical Instruments Co., Ltd; and Stopwatch, JS-60 ltype, manufactured by Shenzhen Junsd Industry Co., Ltd.

Experimental Method and Outcomes

Part One Primary Pharmacodynamic Researches

I. Effects of Capsules of the Present Invention on Mice of Reserpine Depression Model (I) Effects of Capsules of the Present Invention on Behaviour and Body Temperature of Mice of Reserpine Depression Model (1) Capsules of the present invention notably antagonize ptosis and akinesia of mice of reserpine depression model.

1. Method: ICR male mice (SPF-grade, having a body weight of 17-20 g) were stochastically divided into seven groups according to the body weight, and the administration dosages can be found in Table 1. The animals in the groups of administration with a drug were administered by gavage for 22 consecutive days. The normal control group and the reserpine control group were administered by gavage with isovolumetric distilled water (0.2 ml/10 g body weight). 2 mg/kg body weight of reserpine was administered by intraperitoneal injection on the $22^{nd}$ day. After 1 h, 2 h and 6 h of injection of reserpine, animals were placed on a bracket and under observation for 15 s to record the number of animals that closed the eyelids (wherein "−" represents open eyelids; "±" represents semi-open eyelids; and "+" represents close eyelids). Rank sum test was used to compare the difference in eyelids closing between reserpine control group and other groups, and the results can be found in Tables 1, 2 and 3. At 2 h, 4 h, and 6 h after the administration of reserpine, animals were placed at the center of a piece of circular white paper with a diameter of 7.5 cm and under observation for 15 s to record the number of animals that still remained within the circle in 15 s. Then $\chi^2$ (Fisher's Exact Test) was used for the statistical comparison (XU Shuyun, Pharmacology Research Methodology, 3rd Edition, Beijing, p 807 and p 809). The results are shown in Tables 4, 5 and 6.

TABLE 1

Effects of capsules of the present invention on the eyelids closing caused by reserpine

| Group | dosage g/kg body weight | Number of animals | Number of animals which close the eyelids at 1 h after the administration | | | P value |
|---|---|---|---|---|---|---|
| | | | − | ± | + | |
| Normal control | — | 15 | 14 | 1 | 0 | <0.01 |
| Reserpine control | — | 18 | 3 | 7 | 8 | |
| Reserpine + capsules of the present invention | 1.25 | 14 | 0 | 8 | 6 | >0.05 |
| Reserpine + capsules of the present invention | 2.5 | 15 | 3 | 10 | 2 | >0.05 |
| Reserpine + capsules of the present invention | 5.0 | 15 | 5 | 10 | 0 | <0.05 |
| Reserpine + Fluose fine hydrochloride | 0.014 | 15 | 7 | 8 | 0 | <0.01 |
| Reserpine + amitriptyline | 0.050 | 15 | 4 | 10 | 1 | >0.05 |

Notes:
P value represents the comparison with the reserpine control group

TABLE 2

Effects of capsules of the present invention on the eyelids closing caused by reserpine

| Group | dose g/kg body weight | Number of animals | − | ± | + | P value |
|---|---|---|---|---|---|---|
| Normal control | — | 15 | 15 | 0 | 0 | <0.01 |
| Reserpine control | — | 18 | 0 | 3 | 15 | |
| Reserpine + capsules of the present invention | 1.25 | 14 | 0 | 4 | 10 | >0.05 |
| Reserpine + capsules of the present invention | 2.5 | 15 | 2 | 5 | 8 | >0.05 |
| Reserpine + capsules of the present invention | 5.0 | 15 | 4 | 8 | 3 | <0.01 |
| Reserpine + Fluose fine hydrochloride | 0.014 | 15 | 5 | 6 | 4 | <0.01 |
| Reserpine + amitriptyline | 0.050 | 15 | 2 | 11 | 2 | <0.01 |

Notes:
P value represents the comparison with the reserpine control group

TABLE 3

Effects of capsules of the present invention on the eyelids closing caused by reserpine

| Group | dosage g/kg body weight | Number of animals | − | ± | + | P value |
|---|---|---|---|---|---|---|
| Normal control | — | 15 | 15 | 0 | 0 | <0.01 |
| Reserpine control | — | 18 | 0 | 4 | 14 | |
| Reserpine + capsules of the present invention | 1.25 | 14 | 0 | 3 | 11 | >0.05 |
| Reserpine + capsules of the present invention | 2.5 | 15 | 1 | 10 | 4 | <0.01 |
| Reserpine + capsules of the present invention | 5.0 | 15 | 0 | 11 | 4 | <0.01 |
| Reserpine + Fluose fine hydrochloride | 0.014 | 15 | 2 | 11 | 2 | <0.01 |
| Reserpine + amitriptyline | 0.050 | 15 | 0 | 12 | 3 | <0.01 |

Notes:
P value represents the comparison with the reserpine control group

Results:

From Tables 1, 2 and 3, in the 5.0 g/kg body weight dosage group, the administration of capsules of the present invention for consecutive 22 days can notably antagonize ptosis caused at 1-6 h after the intraperitoneal (ip) administration of 2 mg/kg body weight of reserpine (as compared with the reserpine model group, p<0.05 or p<0.01). The minimum effective dosage of capsules of the present invention for antagonizing reserpine-induced ptosis is 2.50 g/kg body weight, and the effect is positively related to the dosage. Both positive control drugs, i.e. fluose fine hydrochloride in a dosage of 14 mg/kg body weight and amitriptyline in a dosage of 50 mg/kg body weight, are antagonistic against reserpine-induced ptosis (P<0.01).

TABLE 4

Effects of capsules of the present invention on the "excircle" behaviour of mice treated with reserpine

| Group | dosage g/kg body weight | Number of animals | Excircle (+) | Within circle (−) | P value |
|---|---|---|---|---|---|
| Normal control | — | 15 | 15 | 0 | >0.05 |
| Reserpine control | — | 18 | 18 | 0 | |
| Reserpine + capsules of the present invention | 1.25 | 14 | 14 | 0 | >0.05 |
| Reserpine + capsules of the present invention | 2.5 | 15 | 15 | 0 | >0.05 |
| Reserpine + capsules of the present invention | 5.0 | 15 | 15 | 0 | >0.05 |
| Reserpine + Fluose fine hydrochloride | 0.014 | 15 | 15 | 0 | >0.05 |
| Reserpine + amitriptyline | 0.050 | 15 | 15 | 0 | >0.05 |

Notes:
P value represents the comparison with the reserpine control group

TABLE 5

Effects of capsules of the present invention on the "excircle" behaviour of mice treated with reserpine

| Group | dose g/kg body weight | Number of animals | Excircle (+) | Within circle (−) | P value |
|---|---|---|---|---|---|
| Normal control | — | 15 | 15 | 0 | <0.01 |
| Reserpine control | — | 18 | 8 | 10 | |
| Reserpine + capsules of the present invention | 1.25 | 14 | 9 | 5 | >0.05 |
| Reserpine + capsules of the present invention | 2.5 | 15 | 14 | 1 | <0.01 |
| Reserpine + capsules of the present invention | 5.0 | 15 | 15 | 0 | <0.05 |
| Reserpine + Fluose fine hydrochloride | 0.014 | 15 | 15 | 0 | <0.01 |
| Reserpine + amitriptyline | 0.050 | 15 | 13 | 2 | <0.05 |

Notes:
P value represents the comparison with the reserpine control group

TABLE 6

Effects of capsules of the present invention on the "excircle" behaviour of mice treated with reserpine

| Group | dosage g/kg body weight | Number of animals | Excircle (+) | Within circle (−) | P value |
|---|---|---|---|---|---|
| Normal control | — | 15 | 15 | 0 | <0.01 |
| Reserpine control | — | 18 | 8 | 10 | |
| Reserpine + capsules of the present invention | 1.25 | 14 | 5 | 9 | >0.05 |

TABLE 6-continued

Effects of capsules of the present invention on the
"excircle" behaviour of mice treated with reserpine

| Group | dosage g/kg body weight | Number of animals | Number of animals that have excircle behaviors at 6 h | | P value |
|---|---|---|---|---|---|
| | | | Excircle (+) | Within circle (−) | |
| Reserpine + capsules of the present invention | 2.5 | 15 | 8 | 7 | >0.05 |
| Reserpine + capsules of the present invention | 5.0 | 15 | 12 | 3 | >0.05 |
| Reserpine + Fluose fine hydrochloride | 0.014 | 15 | 14 | 1 | <0.01 |
| Reserpine + amitriptyline | 0.050 | 15 | 13 | 2 | <0.05 |

Notes:
P value represents the comparison with the reserpine control group

From Tables 4, 5 and 6, for the 2.5-5.0 g/kg body weight dosage groups, the administration of capsule soup of the present invention for 22 consecutive days can notably antagonize akinesia caused at 4 h after intraperitoneal injection of 2 mg/kg body weight of reserpine, and remarkably increase the number of excircle animals ($P<0.05$). The positive control drugs, i.e. fluose fine hydrochloride in a dosage of 14 mg/kg body weight and amitriptyline in a dosage of 50 mg/kg body weight, can notably increase the "excircle" rate of reserpine mice ($P<0.05$ or $P<0.01$).

(2) Capsules of the Present Invention Notably Antagonize the Fall of Body Temperature of Mice of Reserpine Depression Model.

1. Method: ICR male mice (SPF-grade, having a body weight of 18-22 g) were stochastically divided into seven groups according to the body weight, and the dosages administrated are shown in Table 7. The animals in the groups of administration with a drug were administered for 22 consecutive days, and the basal body temperature (rectal temperature) of the animals was measured before administration on the $22^{nd}$ day. During the administration, 2 mg/kg body weight of reserpine was administered by intraperitoneal injection. The rectal temperatures were measured at 6 h and 24 h after the administration of reserpine. The difference values of body temperature before and after administration and the difference values of their own body temperatures were calculated so as to conduct the statistical comparison by single factor analysis of variance (H. G Vogel & W. H. Vogel, Drug Discovery and Evaluation □Guidance for Pharmacological Assays, translated by D U Guanhua et al, [M] Beijing: Science Press, 2001.409,412). The results can be found in Tables 7 and 8.

TABLE 7

Effects of capsules of the present invention on the body temperature of mice treated with reserpine

| Group | dosage g/kg body weight | Number of animals | Body temperature (° C.) | | |
|---|---|---|---|---|---|
| | | | Body temperature before modeling | 6 h after making models | 24 h after making models |
| Normal control | — | 15 | 36.47 ± 0.36** | 35.94 ± 0.52** | 37.56 ± 0.72** |
| Reserpine control | — | 18 | 37.24 ± 0.78 | 32.62 ± 1.42 | 35.98 ± 0.79 |
| Reserpine + capsules of the present invention | 1.25 | 14 | 37.09 ± 0.53 | 31.92 ± 2.07 | 36.44 ± 0.51 |
| Reserpine + capsules of the present invention | 2.5 | 15 | 37.39 ± 0.57 | 33.74 ± 1.25* | 36.53 ± 0.71* |
| Reserpine + capsules of the present invention | 5.0 | 15 | 37.28 ± 0.49 | 33.74 ± 0.67* | 36.49 ± 0.74 |
| Reserpine + Fluose fine hydrochloride | 0.014 | 15 | 37.66 ± 0.725 | 35.0 ± 0.87** | 35.39 ± 0.63 |
| Reserpine + amitriptyline | 0.050 | 15 | 36.74 ± 0.87 | 34.36 ± 1.12** | 35.85 ± 3.36 |

Notes:
as compared with reserpine model group,
*$P < 0.05$ and
**$P < 0.01$

TABLE 8

Effects of capsules of the present invention on the body temperature of mice of reserpine depression model ($\bar{x} \pm s$)

| Group | dosage g/kg body weight | Number of animals | Body temperature difference (° C.) | |
|---|---|---|---|---|
| | | | 6 h after making models | 24 h after making models |
| Normal control | — | 15 | 0.53 ± 0.60** | −1.13 ± 0.74* |
| Reserpine control | — | 18 | 4.62 ± 1.52 | 1.26 ± 1.18 |
| Reserpine + capsules of the present invention | 1.25 | 14 | 5.16 ± 1.97 | 0.65 ± 0.75 |
| Reserpine + capsules of the present invention | 2.5 | 15 | 3.65 ± 1.35 | 0.86 ± 0.90 |

TABLE 8-continued

Effects of capsules of the present invention on the body temperature of mice of reserpine depression model ($\bar{x} \pm s$)

| Group | dosage g/kg body weight | Number of animals | Body temperature difference (° C.) | |
|---|---|---|---|---|
| | | | 6 h after making models | 24 h after making models |
| Reserpine + capsules of the present invention | 5.0 | 15 | 3.54 ± 0.70* | 0.79 ± 0.97 |
| Reserpine + Fluose fine hydrochloride | 0.014 | 15 | 2.66 ± 1.11** | 2.27 ± 1.00* |
| Reserpine + amitriptyline | 0.050 | 15 | 2.38 ± 1.30** | 0.89 ± 3.58 |

Notes:
as compared with reserpine model group, *P < 0.05 and **P < 0.01.
Body temperature value difference = body temperature value after the administration − body temperature before the administration 2. Results:

Tables 7 and 8 indicate that for the 2.5-5.0 g/kg body weight group, the administration of the soup of the capsule of the present invention for 22 consecutive days can notably antagonize the fall in body temperature caused at 6 h and 24 h after intraperitoneal injection of 2 mg/kg body weight of reserpine (as compared with reserpine model group, P<0.05 and P<0.001). The minimum effective dose is 2.5 g/kg body weight. Both positive control drugs, i.e. fluose fine hydrochloride in a dosage of 14 mg/kg body weight and amitriptyline in a dosage of 50 mg/kg body weight, can notably antagonize the fall in body temperature of mice caused by reserpine (as compared with reserpine model group, P<0.01)

(II) Effects of Capsules of the Present Invention on the Level of Monoamine Neurotransmitters in the Brain of Mice of Reserpine Depression Model 1. Method: ICR male mice; and the groups and administration doses can be found in Table 9. The animals in the groups of administration with a drug were administered by gavage for 25 consecutive days. The normal control group and reserpine control group were administered with isovolumetric distilled water. On the 23$^{rd}$ day of the test, 1 mg/kg body weight of reserpine was ip administered for each group except the normal control group, and each group receiving reserpine was administered once more. At 1 hour after the last administration of reserpine, the heads of mice were cut off and the brain tissues were taken out, frozen with dry ice and preserved at −20□. The content of noradrenaline (NA), dopamine (DA) and 5-hydroxytryptamine (5-HT) in the cerebellar tissue homogenate was measured respectively by means of fluorophotometry. Each group of data were statistically processed by single factor analysis of variance, and the results are shown in Table 9.

TABLE 9

Effects of capsules of the present invention on NA, DA and 5-HT in the brain tissue of reserpine mice ($\bar{x} \pm s$)

| Group | dosage g/kg body weight | Number of animals | NA (ng/g) | DA (ng/g) | 5-HT (ng/g) |
|---|---|---|---|---|---|
| | | 9 | 698.99 ± 225.41** | 1192.98 ± 300.61 | 718.01 ± 89.90** |
| Reserpine control | — | 13 | 299.92 ± 267.08 | 1439.34 ± 357.33 | 492.01 ± 192.80[L] |
| Reserpine + capsules of the present invention | 1.25 | 7 | 579.73 ± 595.50 | 1848.58 ± 713.98 | 467.45 ± 355.45 |
| Reserpine + capsules of the present invention | 2.5 | 8 | 880.45 ± 428.81** | 2305.99 ± 530.37** | 781.43 ± 135.10** |
| Reserpine + capsules of the present invention | 5.0 | 9 | 875.98 ± 449.33** | 2169.99 ± 278.19** | 597.60 ± 436.10 |
| Reserpine + Fluose fine hydrochloride | 0.01 | 5 | 1326.48 ± 670.50** | 1967.20 ± 562.57** | 707.25 ± 115.94* |
| Reserpine + amitriptyline | 0.050 | 8 | 1023.46 ± 619.56** | 1806.61 ± 275.37* | 557.57 ± 174.75 |

Notes:
as compared with reserpine control group,
*P < 0.01 and
**P < 0.05;
as compared with the normal control group, ΔP < 0.05

2. Results

From Table 9, it can be seen that 2.5-5.0 g/kg body weight of capsules of the present invention can notably antagonize NA content decrease in the brain tissue caused by reserpine and increase the DA content. Moreover, the 2.5 g/kg body weight dosage group also notably antagonizes the 5-HT content decrease in the brain tissue caused by reserpine (as compared with reserpine control group, P<0.05, or P<0.01). The positive control drug—amitriptyline in a dose of 50 mg/kg body weight can notably enhance the level of NA and DA in the brain tissue of mice treated with reserpine (as compared with reserpine control group, P<0.05, or P<0.01).

(III) Effects of Capsules of the Present Invention on the Level of Monoamine Neurotransmitters in the Brains of Normal Mice 1. Method: ICR male mice; and the groups and administration doses can be found in Table 10. The animals in the groups of administration with a drug were administered by gavage for 25 consecutive days. At 80 min after the final administration, the heads of mice were cut off and the brain tissues were taken out, frozen with dry ice and preserved at −20□. The content of noradrenaline (NA), dopamine (DA) and 5-hydroxytryptamine (5-HT) in the whole brain homogenate without cerebellum was measured respectively by means of the fluorophotometry[2]. The data were statistically processed by single factor analysis of variance, and the results are shown in Table 10.

2. Extraction of monoamine neurotransmitters in brain tissue and measurement of the neurotransmitters by means of fluorophotometry (KUANG Peigen, ZHOU Xinfu and XU Bo, Extraction of Monoamine Neurotransmitters in Brain Tissue and Measurement of the Neurotransmitters by Means of Fluorophotometry, Academic Journal of PLA Postgraduate Medical School, 1982, 3(2) 181-185).

(1) Treatment of Brain Tissue of Mice and Homogenization

At the end of the test, the heads of mice were rapidly cut off and the brain tissues were immediately taken out, promptly frozen with dry ice and moved into a refrigerator having a temperature of −20□. The tissue was defreezed before homogenization. The cerebellum, medulla oblongata and olfactory bulb were removed, and then 300 mg brain tissue was weighed with a analytical balance. Then 10 times amount by volume of acidic n-butanol (prepared by saturating 100 ml re-steamed n-butanol with NaCl, and mixing with 0.85 ml strong hydrochloric acid) were added into the brain tissue for homogenization.

(2) Extraction of NA, DA and 5-HT

The brain tissue homogenate was centrifugated (2,000 rpm) for 5 min. Then 2.5 ml supernatant was taken out and placed in centrifuge tube with a plug containing 1 ml 0.1N HC1 and 5 ml n-heptane. The centrifuge tube was placed on the KS vibrator, oscillated for 5 min and centrifugated (2,500 rpm) for 5 min. 6 to ml upper organic phase was placed into the tube having a plug and containing 0.6 ml 0.033 M NaHCO$_3$ so as to extract 5-HIAA. Then 0.5 ml and 0.4 ml were respectively taken out from the lower aqueous phase, wherein the former was used to measure NA and DA, and the latter was used to measure 5-HT.

Internal standard tube treatment: 9 ml of the acidic n-butanol homogenate was averagely divided into 3 tubes, to two of them, 40 μl mixed standard solution (respectively containing 5 μg/ml standard substances of NA, DA and 5-HT) was added.

(3) Measurement: The fluorophotometry was conducted on NA, DA and 5-HT (KUANG Peigen, ZHOU Xinfu and XU Bo, Extraction of Monoamine Neurotransmitters in Brain Tissue and Measurement of the Neurotransmitters by Means of Fluorophotometry, Academic Journal of PLA Postgraduate Medical School, 1982, 3(2) 181-185).

TABLE 10

Effects of capsules of the present invention on NA, DA and 5-HT in the brain tissue of nomal mice ($\bar{x} \pm s$)

| Group | dosage g/kg body weight | Number of animals | NA (ng/g) | DA (ng/g) | 5-HT (ng/g) |
|---|---|---|---|---|---|
| Normal control | — | 13 | 578.81 ± 204.97 | 1426.98 ± 347.16 | 537.54 ± 104.44 |
| Capsules of the present invention | 1.25 | 15 | 757.97± | 1856.40 ± 439.62** | 700.03 ± 279.90* |
| Capsules of the present invention | 2.5 | 14 | 654.20 ± 325.36 | 1616.74 ± 583.29 | 857.14± |
| Capsules of the present invention | 5.0 | 14 | 702.94 ± 191.74 | 1474.46 ± 501.86 | 950.31± |
| Fluose fine hydrochloride | 0.01 | 13 | 896.46± | 1432.52 ± 395.77 | 841.85± |
| Amitriptyline | 0.05 | 13 | 803.54± | 1519.29 ± 373.72 | 1015.17± |

Notes:
as compared with the normal control goup,
*P < 0.05 and
**P < 0.01.

3. Results

Table 10 above indicates that for 1.25-5.0 g/kg body weight dosage group, the administration of capsules of the present invention via gavage for 25 consecutive days can notably increase the level of 5-HT in the brain tissue of mice. (as compared with the normal control group, P<0.05, or P<0.01), and the effect is positively related to the dosage. The positive control drugs, i.e. amitriptyline and fluose fine hydrochloride, can also notably increase the level of 5-HT in the brain tissue (as compared with the normal control group, P<0.01). For the 1.25 g/kg body weight dosage group of administration of capsules of the present invention, the level of NA and DA was notably increased in the brain tissue. The positive control drugs, i.e. amitriptyline and fluose fine hydrochloride, can also increase the level of NA and DA in the brain tissue (as compared with the normal control group, P<0.01).

(IV) Effects of Capsules of the Present Invention on Shaking-Head Behavior Induced by 5-hydroxytryptophane (5-HTP)

1. Principle: according to the monoamine hypothesis on the occurrence of depression, the function of antidepressant lies in that it can enhance the functions of the noradrenergic and/or serotonergic nerve. A great variety of antidepressant may enhance the effect of 5-HT by blocking the reuptake of 5-HT. 5-HTP may be used as a precursor of 5-HT, and monoamine oxidase inhibitor—pargyline hydrochloride may inhibit the enzymatic degradation thereof. The characteristic symptom—shaking-head behavior is obvious on mice. The enhancement of shaking-head behavior of mice after administration of the test drug may be used as an evidence to the fact that the inhibition of 5-HT uptaking function is the anti-depression mechanism.

2. Method: ICR male mice (20±1 g) were stochastically divided into seven groups according to the body weight, and each group comprises 12 animals. The groups and administration doses are shown in Table 14. The animals in the groups of administration with a drug were consecutively administered by gavage for 21 days. On the 21$^{St}$ day of the test, each group were administered with 75 mg/kg body weight of pargyline hydrochloride by subcutaneous injection, and timing was started. Except the normal control group, other groups were administered with 20 mg/kg body weight of 5-HTP by intraperitoneal injection 90 min after injection of pargyline; and the times of shaking-head behavior were recorded in the following 10 minutes. The data were then statistically compared by single factor analysis of variance, and the results are shown in Table 11.

TABLE 11

The enhancement of 5-HTP in mice caused by the capsules of the present invention

| Group | dosage g/kg body weight | Number of animals | times of shaking-head behavior (animals · min) |
|---|---|---|---|
| Normal control | — | 10 | 0 |
| 5-HTP model | — | 16 | 18.38 ± 16.14 |
| Capsules of the present invention | 1.25 | 10 | 25.44 ± 22.57 |
| Capsules of the present invention | 2.5 | 11 | 18.64 ± 18.13 |
| Capsules of the present invention | 5.0 | 10 | 13.20 ± 6.32 |
| Capsules of the present invention | 10.0 | 10 | 37.11 ± 17.29* |
| Fluose fine hydrochloride | 0.014 | 10 | 125.80 ± 64.0*** |

Notes:
as compared with 5-HTP model group, p < 0.01, or P < 0.01.

3. Results

Table 11 above indicates that the administration of 10.0 g/kg body weight powder of the capsule of present invention can notably increase the times of shaking-head behavior of mice (P<0.05, as compared with the model group). The positive control drug—14 mg/kg body weight of fluose fine hydrochloride can notably increase the times of 5-HTP-induced shaking-head behavior of mice (as compared with the 5-HTP model group, P<0.01).

Part Two Auxiliary Pharmacodynamic Researches

I. Analgetic Effects of Capsules of the Present Invention on Mice (Hot Plate Method)

1. Method:

ICR female mice having a body weight of 18-22 g were stochastically divided into six groups according to the body weight. Before test, the temperature of the aqueous thermostat was controlled at 56±0.5□. One mouse was placed on the hot plate each time, and the time of licking postpedes was defined as the pain threshold of said mouse. The mice which licked postpedes for less than 5 s or more than 30 s or jumped were abandoned. The normal pain thresholds were measured again. The average value of two normal pain thresholds was used as the pain threshold of the mouse before administration. The selected mice were used for the test and stochastically divided into six groups, including the group of 10 g/kg body weight capsules of the present invention, the group of 5 g/kg body weight capsules of the present invention, the group of 2.5 g/kg body weight capsules of the present invention, the group of 1.25 g/kg body weight capsules of the present invention, the aspirin group (0.33 g/kg body weigh), and the normal control group (administered with isovolumetric normal saline). There were 22 mice in the normal control group, and there were 11 mice in each of other groups. Six groups of mice were consecutively administered by gavage for 3 days, and postpedes licking was timed at 1 h, 3 h and 5 h after the last administration by gavage. The data were verified between the groups by single factor analysis of variance, and the results are shown in Table 12.

TABLE 12

Analgetic Effects of capsules of the present invention on normal mice (hot plate method)

| Group | dosage g/kg body weight | Number of animals | Pain threshold (S) | | |
|---|---|---|---|---|---|
| | | | 1 h after admi. | 3 h after admi. | 5 h after admi. |
| Normal control | — | 22 | 13.55 ± 3.38 | 14.64 ± 4.78 | 13.77 ± 4.79 |
| Capsules of the present invention | 1.25 | 11 | 14.91 ± 6.41 | 16.00 ± 7.69 | 16.27 ± 6.05 |
| Capsules of the present invention | 2.5 | 11 | 25.00 ± 19.57 | 25.36 ± 14.21* | 23.73 ± 11.50* |
| Capsules of the present invention | 5.0 | 11 | 14.36 ± 5.35 | 20.36 ± 8.03* | 21.91 ± 11.61* |
| Capsules of the present invention | 10.0 | 11 | 23.18 ± 10.28** | 28.09 ± 14.62** | 30.73 ± 12.31** |
| Aspirin group | 0.33 | 11 | 18.27 ± 12.52 | 15.27 ± 2.57 | 16.09 ± 4.70 |

Notes:
as compared with the normal control group,
**P < 0.01,
*P < 0.05.

2. Results

The results in Table 12 above indicate that the group of 10 g/kg body weight capsules of the present invention can notably increase the duration of hot plate-caused pain (as compared with the normal control group, P<0.01) after 1 h, 3 h and 5 h of administration. The groups of 5 g/kg body weight and 2.5 g/kg body weight capsules of the present invention can also increase the pain threshold values of mice (as compared with the normal control group, P<0.05) at 3 h and 5 h after administration. See the Table 12. The minimum effective analgetic dosage of capsules of the present invention was 2.5 g/kg body weight II. Effects of Capsules of the Present Invention on Pain Caused by Administration of Acetic Acid to Mice by Intraperitoneal Injection (Stretching Method)

1. Method: ICR mice having a body weight of 18-22 g, half male and half female, were randomly divided into five groups according to the body weight, including the group of 5 g/kg body weight capsules of the present invention, the group of 2.5 g/kg body weight capsules of the present invention, the group of 1.25 g/kg body weight capsules of the present invention, the aspirin group (0.33 g/kg body weigh), and the normal control group (administered with isovolumetric normal saline). There were 19 mice in the normal control group, and there were 10-11 mice in each of other groups. The animals in the groups of administration with a drug were consecutively administered for 3 days by gavage. Except the normal control group, each mouse in other groups was administered by intraperitoneal injection with 0.1 ml/10 g body weight 0.6% glacial acetic acid at 1 h after the final administration. Then the times of stretching caused by glacial acetic acid during 15 minutes after injection were recorded. The test data were statistically processed according to the T verification between the groups, and the results are shown in Table 13.

TABLE 13

Effects of capsules of the present invention on stretching caused by acetic acid

| Group | Dosage (g/kg body weight) | Number of animals | Stretching times |
|---|---|---|---|
| Model control | — | 19 | 32.79 ± 10.34 |
| Capsules of the present invention | 1.25 | 11 | 29.79 ± 10.68 |
| Capsules of the present invention | 2.5 | 10 | 21.20 ± 8.56* |
| Capsules of the present invention | 5.0 | 11 | 20.27 ± 7.43** |
| Aspirin group | 0.33 | 11 | 12.00 ± 9.20** |

Notes:
as compared with the model control group, **P < 0.01, *P < 0.05.

2. Results

Table 13 above indicates that the groups of 5 g/kg body weight and 2.5 g/kg body weight capsules of the present invention can notably decrease the stretching times caused by acetic acid (as compared with the model control group, P<0.01 or P<0.05).

III. Synergistic Effects of Capsules of the Present Invention with Sodium Pentobarbital on Sleeping 1. Method: ICR mice having a body weight of 18-22 g, half male and half female, were randomly divided into five groups according to the body weight (see Table 14 for details). The animals in the groups of administration with a drug were consecutively administered for 7 days by gavage. Mice were weighed before the last administration, and administered by intraperitoneal injection with 35 mg/kg body weight sodium pentobarbital at 1 h after the last administration. The number of animals falling asleep was recorded. The data were then statistically processed according to the $\chi^2$ verification, and the results are shown in Table 14.

TABLE 14

Effects of capsules of the present invention on the rate of falling asleep caused by the intraperitoneal injection of sodium pentobarbital

| Group | dosage g/kg body weight | Sodium pentobarbital dosage mg/kg body weight | Number of animals | Falling asleep | Not falling asleep | P value |
|---|---|---|---|---|---|---|
| Sodium pentobarbital group | — | 35 | 16 | 9 | 7 | |
| Capsules of the present invention | 1.25 | 35 | 11 | 5 | 6 | P > 0.05 |
| Capsules of the present invention | 2.5 | 35 | 11 | 5 | 6 | P > 0.05 |
| Capsules of the present invention | 5.0 | 35 | 11 | 4 | 7 | P > 0.05 |
| Aspirin group | 0.33 | 35 | 11 | 5 | 6 | P > 0.05 |

Notes:
P value represents the comparison with sodium pentobarbital group.

2. Results

Table 14 above indicates that the dosages of 1.25-5.0 g/kg body weight capsules of the present invention have no synergistic effects with sodium pentobarbital (P>0.05).

Research Conclusion

Currently, reserpine depression model is not only the most widely selected and classical animal model in China, but also the simplest and practicable method for selecting drugs against depression. Reserpine results in insufficient content of the neurotransmitter—5-HT or disfunction thereof, so that the function of NA is weakened and the cholinergic nerve system takes advantage. Animals show the behavious such as ptosis, the fall of body temperature, stiffness and the like, and physiological changes. The aforesaid research results show that the capsules of the present invention can not only alleviate said symptoms, but can also notably adjust the function of monoamine neurotransmitters of central nerves system. The groups of administration with 1.25 g/kg body weight, 2.5 g/kg body weight and 5.0 g/kg body weight capsules of the present invention can all notably antagonize the decrease of NA content in the brain tissue of mice of reserpine depression model, and increase DA level. 2.5 g/kg body weight group can also notably antagonize the decrease of 5-HT content in the brain tissue of mice of reserpine depression model. In the measurement of monoamine neurotransmitters in the brain of the normal mice, the capsules of the present invention at 1.25 g/kg body weight, 2.5 g/kg body weight and 5.0 g/kg body weight dosages can all increase the 5-HT level in the brain tissue of mice, and the effect is positively related to the dosage. In addition, the dosage of 1.25 g/kg body weight capsules of the present invention can also notably increase the NA and DA level in the brain tissue.

The aforesaid results provide a pharmacological basis for the treatment of depression with the traditional Chinese medicinal composition according to the invention. Not to be bound by theories, the capsules of the present invention can bring out the anti-depression effect by adjusting the level of monoamine neurotransmitters (NA, DA, 5-HT) in the central nerves.

The applicant has illustrated the present invention in a complete and detailed manner. The full text or relevant parts of all the publications cited in this application are incorporated into this application by reference.

Obviously, those skilled in the art can make many modifications, amendments and changes to the present invention within the spirit and scope of the present invention, and said modifications, amendments and changes should be covered within the scope of the present invention.

The invention claimed is:

1. A Chinese medicinal composition comprising 120-200 parts by weight of Fructus Gardeniae, 300-500 parts by weight of Fructus Forsythiae, 120-200 parts by weight of Cortex Magnoliae Officinalis, 180-300 parts by weight of Rhizoma Pinelliae 120-200 parts by weight of Fructus Aurantii, 144-240 parts by weight of Poria, 144-240 parts by weight of Caulis Perillae, and 36-60 parts by weight of Radix Glycyrrhizae.

2. The medicinal composition according to claim 1, wherein said composition comprises 160 parts by weight of Fructus Gardeniae, 400 parts by weight of Fructus Forsythiae, 160 parts by weight of Cortex Magnoliae Officinalis, 240 parts by weight of Rhizoma Pinelliae, 160 parts by weight of Fructus Aurantii, 192 parts by weight of Poria, 192 parts by weight of Caulis Perillae, and 48 parts by weight of Radix Glycyrrhizae.

3. The medicinal composition according to claim 1, wherein said composition comprises 120 parts by weight of Fructus Gardeniae, 300 parts by weight of Fructus Forsythiae, 200 parts by weight of Cortex Magnoliae Officinalis, 280 parts by weight of Rhizoma Pinelliae, 190 parts by weight of Fructus Aurantii, 240 parts by weight of Poria, 180 parts by weight of Caulis Perillae, and 55 parts by weight of Radix Glycyrrhizae.

4. The medicinal composition according to claim 1, wherein said composition comprises 200 parts by weight of Fructus Gardeniae, 300 parts by weight of Fructus Forsythiae, 120 parts by weight of Cortex Magnoliae Officinalis, 200 parts by weight of Rhizoma Pinelliae, 120 parts by weight of Fructus Aurantii, 150 parts by weight of Poria, 240 parts by weight of Caulis Perillae, and 40 parts by weight of Radix Glycyrrhizae.

5. The medicinal composition according to claim 1, wherein said composition comprises 160 parts by weight of Fructus Gardeniae, 480 parts by weight of Fructus Forsythiae, 150 parts by weight of Cortex Magnoliae Officinalis, 210 parts by weight of Rhizoma Pinelliae, 160 parts by weight of Fructus Aurantii, 200 parts by weight of Poria, 240 parts by weight of Caulis Perillae, and 60 parts by weight of Radix Glycyrrhizae.

6. The medicinal composition of claim 1, comprising 135-185 parts by weight of Fructus Gardeniae, 310-490 parts by weight of Fructus Forsythiae, 130-180 parts by weight of Cortex Magnoliae Officinalis, 200-280 parts by weight of Rhizoma Pinelliae, 140-190 parts by weight of Fructus Aurantii, 164-230 parts by weight of Poria, 154-230 parts by weight of Caulis Perillae, and 38-58 parts by weight of Radix Glycyrrhizae.

7. The medicinal composition of claim 6, comprising 148-172 parts by weight of Fructus Gardeniae, 380-430 parts by weight of Fructus Forsythiae, 138-175 parts by weight of Cortex Magnoliae Officinalis, 220-260 parts by weight of Rhizoma Pinelliae, 149-175 parts by weight of Fructus Aurantii, 176-220 parts by weight of Poria, 184-220 parts by weight of Caulis Perillae, and 40-55 parts by weight of Radix Glycyrrhizae.

8. A method for preparing the medicinal composition according to claim 1, wherein the preparation of the active components of the medicinal composition comprises the following steps:
   1) weighing each of Fructus Gardeniae, Fructus Aurantii, Cortex Magnoliae Officinalis, and Fructus Forsythiae crushing Fructus Gardeniae, mixing, and extracting the mixture 1-3 times with 50-80% ethanol for 1-3 h each time, filtering each extract and respectively concentrating each filtrate to obtain clear extracts having a relative density of 1.01-1.04, and combining each concentrate;
   2) weighing Poria, Caulis Perillae and Radix Glycyrrhizae, mixing and decocting three times for 1-3 hours each time with water combining each decoction, and concentrating each decoction to obtain a clear extract having a relative density of 1.10-1.15;
   3) weighing Rhizoma Pinelliae, crushing and grinding it into a fine powder; and
   4) combining the powder obtained from step 3) with the clear extracts obtained from steps 1) and 2), and mixing them to obtain a homogenous mixture.

9. A pharmaceutical formulation comprising the medicinal composition according to claim 1, wherein said pharmaceutical formulation is in a form of a capsule, a tablet, a pill, an oral liquor, a soft capsule or a drop pill.

10. The pharmaceutical formulation according to claim 9, wherein the pharmaceutical formulation is in a form of capsules.

11. A method for preparing the pharmaceutical formulation according to claim 10, comprising the following steps:
   1) weighing each of Fructus Gardeniae, Fructus Aurantii, Cortex Magnoliae Officinalis, and Fructus Forsythiae, crushing Fructus Gardeniae, mixing, and extracting the mixture 1-3 times with 50-80% ethanol for 1-3 h each time, filtering each extract and respectively concentrating each filtrate to obtain clear extracts having a relative density of 1.01-1.04, and combining each concentrate;
   2) weighing Poria, Caulis Perillae and Radix Glycyrrhizae, mixing and decocting three times for 1-3 hours each time with water, combining each decoction, and concentrating each decoction to obtain a clear extract having a relative density of 1.10-1.15;
   3) weighing Rhizoma Pinelliae and crushing and grinding it into a fine powder;
   4) combining the powder obtained from step 3) with the clear extracts obtained from steps 1) and 2), and mixing them to obtain a homogenized mixture;
   5) granulating the homogenized mixture of step (4) to obtain a granulated mixture; and 6) adding adjuvants to the granulated mixture of step 5), granulating with an 18 mesh sieve to obtain particles, and filling gelatin capsules with the particles.

12. The method for preparing the pharmaceutical formulation according to claim 11, wherein the granulation in step 5) is conducted by spray drying.

13. A method for preparing the medicinal composition of claim 9, comprising the following steps:
   1) weighing each of Fructus Gardeniae, Fructus Aurantii, Cortex Magnoliae Officinalis, and Fructus Forsythiae, crushing Fructus Gardeniae, mixing, and extracting the mixture 1-3 times with 50-80% ethanol for 1-3 h each time, filtering each extract and respectively concentrating each filtrate to obtain clear extracts having a relative density of 1.01-1.04, and combining each concentrate;
   2) weighing Poria, Caulis Perillae and Radix Glycyrrhizae, mixing and decocting three times for 1-3 hours each time with water, combining each decoction, and concentrating each decoction to obtain a clear extract having a relative density of 1.10-1.15;
   3) weighing Rhizoma Pinelliae and crushing and grinding it into a fine powder;
   4) combining the powder obtained from step 3) with the clear extracts obtained from steps 1) and 2), and mixing them to obtain a homogenized mixture; and
   5) adding adjuvants to the homogenized mixture of step (4), and formulating into a tablet, a pill, an oral liquor, a drop pill or a soft capsule.

14. A method for treating depression, the method comprising administering an effective amount of a medicinal composition to a subject in need thereof, wherein said medicinal composition is prepared by a method comprising
   1) weighing each of Fructus Gardeniae, Fructus Aurantii, Cortex Magnoliae Officinalis, and Fructus Forsythiae, crushing Fructus Gardeniae, mixing, and extracting the mixture 1-3 times with 50-80% ethanol for 1-3 h each time, filtering each extract and respectively concentrating each filtrate to obtain clear extracts having a relative density of 1.01-1.04, and combining each concentrate;
   2) weighing Poria, Caulis Perillae and Radix Glycyrrhizae, mixing and decocting three times for 1-3 hours each time with water, combining each decoction, and concentrating each decoction to obtain a clear extract having a relative density of 1.10-1.15;
   3) weighing Rhizoma Pinelliae and crushing and grinding it into a fine powder;
   4) combining the powder obtained from step 3) with the clear extracts obtained from steps 1) and 2), and mixing them to obtain a homogenized mixture.

15. The method of claim 14, wherein the method for preparing said medicinal composition further comprises:
   5) granulating the homogenized mixture of step 4) to obtain a granulated mixture; and
   6) adding adjuvants to the granulated mixture of step 5), granulating with an 18 mesh sieve to obtain particles, and filling gelatin capsules with the particles.

16. The composition of any one of claims 1, 2, 3, 4, 5, 9, 10, 6, or 7, wherein said Rhizoma Pinelliae is either a) dried rhizome of Pinelliae or b) Rhizoma Pinelliae prepared by steeping Rhizoma Pinelliae in boiling water, adding fresh ginger to the boiling water, adding Alum and decocting, removing the Rhizoma Pinelliae and drying and slicing the Rhizoma Pinelliae; and wherein said Cortex Magnoliae Officinalis is either a) dried bark of Magnolia officinalis or b) Cortex Magnoliae Officinalis prepared by homogeneously mixing Cortex Magnoliae Officinalis shreds with ginger juice and stir-frying to the extent that ginger juice is completely absorbed by the Cortex Magnoliae Officinalis shreds, removing the Cortex Magnoliae Officinalis shreds and drying them.

17. The method of any one of claims 8, 11, 13, or 14, wherein said Rhizoma Pinelliae is either a) dried rhizome of Pinelliae or b) Rhizoma Pinelliae prepared by steeping Rhizoma Pinelliae in boiling water, adding fresh ginger to the boiling water, adding Alum and decocting, removing the Rhizoma Pinelliae and drying and slicing the Rhizoma Pinelliae; and wherein said Cortex Magnoliae Officinalis is either a) dried bark of Magnolia officinalis or b) Cortex Magnoliae Officinalis prepared by homogeneously mixing Cortex Magnoliae Officinalis shreds with ginger juice and stir-frying to the extent that ginger juice is completely absorbed by the Cortex Magnoliae Officinalis shreds, removing the Cortex Magnoliae Officinalis shreds and drying them.

18. The method of any one of claims 8, 11, 13, or 14, wherein, in step (1), the extractions are conducted using a 6-10 fold amount of 50%-80% ethanol.

19. The method of any one of claims 8, 11, 13, or 14, wherein step (2) comprises weighing Poria, Caulis Perillae and Radix Glycyrrhizae, mixing and decocting three times, wherein a first time of decocting is conducted using an 8-10 fold amount of water.

20. The method of claim 19, wherein step (2) comprises weighing Poria, Caulis Perillae and Radix Glycyrrhizae, mixing and decocting three times, wherein a first time of decocting is conducted using an 8-10 fold amount of water, and a second time and a third time of decocting are each conducted using a 6-8 fold amount of water.

* * * * *